(12) United States Patent
Lakner et al.

(10) Patent No.: US 7,439,250 B2
(45) Date of Patent: Oct. 21, 2008

(54) COMPOSITIONS AND METHODS RELATED TO FATTY AMINO ACID DERIVATIVES

(75) Inventors: Frederick J. Lakner, San Diego, CA (US); George R. Negrete, San Antonio, TX (US)

(73) Assignee: Board of Regents, The University of Texas System, Austin, TX (US)

(*) Notice: Subject to any disclaimer, the term of this patent is extended or adjusted under 35 U.S.C. 154(b) by 612 days.

(21) Appl. No.: 10/715,331

(22) Filed: Nov. 17, 2003

(65) Prior Publication Data

US 2004/0192894 A1   Sep. 30, 2004

Related U.S. Application Data

(60) Provisional application No. 60/426,686, filed on Nov. 15, 2002.

(51) Int. Cl.
*C07D 239/06* (2006.01)
*A61K 31/513* (2006.01)

(52) U.S. Cl. .................. 514/269; 544/319
(58) Field of Classification Search .......... 544/319; 514/269

See application file for complete search history.

(56) References Cited

OTHER PUBLICATIONS

Chu et al., "Enantiomerically pure dihydropyrimidinones as reagents and auxiliaries for asymmetric synthesis," *J. Am. Chem. Soc.*, 114:1800-1812, 1992.
Corbett and Gleason, "Preparation of active esters on solid support for aqueous-phase pepetide couplings," *Tetrahedron Letters*, 43:1369-1372, 2002.
Hardy and Samworth, "Use of NN'-isoproplidene dipoptides in peptide synthesis," *J. Chem. Soc.*, [Perkin 1]17:1954-1960, 1977.

*Primary Examiner*—Deepak Rao
(74) *Attorney, Agent, or Firm*—Fulbright & Jaworski, LLP

(57) ABSTRACT

The present invention concerns the use of methods and/or compositions related to the synthesis and use of fatty asparagine, cysteine and/or serine derivatives. In particular, the invention concerns methods and compositions for the production of liposomes including fatty asparagine, cysteine and/or serine derivatives.

13 Claims, 1 Drawing Sheet

COMPOSITIONS AND METHODS RELATED TO FATTY AMINO ACID DERIVATIVES

BACKGROUND OF THE INVENTION

This application claims priority to U.S. Provisional Patent Application Ser. No. 60/426,686 filed on Nov. 15, 2002, which is incorporated herein in its entirety by reference.

This invention was made with government support under grant number GM08194-SO6 awarded by the National Institute of General Medical Sciences. The government has certain rights in the invention.

1. FIELD OF THE INVENTION

The present invention relates generally to the fields of chemistry and biochemistry. More particularly, it concerns methods and compositions for the synthesis and use of fatty amino acid derivatives.

2. DESCRIPTION OF RELATED ART

Amphiphiles are molecules such as surfactants or lipids that have a polar head group (hydrophilic) attached to nonpolar hydrophobic alkyl chains. Because of this characteristic they self-assemble in water and give rise to a wide range of phases with different structures and properties. Aqueous dispersions of amphiphiles are present in every aspect of day-to-day life, e.g., forming biological cell membranes, stabilizing emulsified food, or being used as soap.

In 1965, Alex Bangham and coworkers discovered that dried films of phosphatidylcholine spontaneously formed closed bimolecular leaflet vesicles upon hydration. Eventually, these structures came to be known as liposomes. A number of uses for liposomes have been proposed in medicine. Some of these uses are as carriers to deliver therapeutic agents to target organs. The agents are encapsulated during the process of liposome formation and released in vivo when liposomes fuse with the lipids of cell surface membrane. Liposomes provide a means of delivering higher concentrations of therapeutic agents to target organs. Further, since liposomal delivery focuses therapy at the site of liposome uptake, it reduces toxic side effects.

For example, some liposomal drugs are several hundred-fold more effective than the free drug in treating leishmaniasis. Liposome-entrapped amphotericin B appears to be more effective than the free drug in treating immunosuppressed patients with systemic fungal disease. Other uses for liposome encapsulation include restriction of doxorubicin toxicity and diminution of aminoglycoside toxicity.

SUMMARY OF THE INVENTION

Various embodiments of the invention includes compositions and methods relating to a fatty asparagine, serine and/or cysteine derivatives. In certain embodiments, an asparagine derivative, or carboxylate salt thereof, of the formulas:

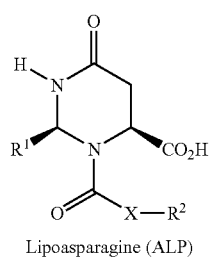

Lipoasparagine (ALP)

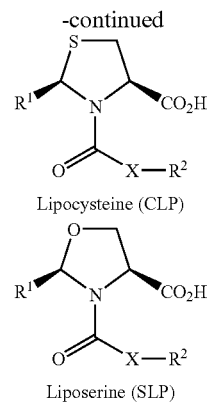

Lipocysteine (CLP)

Liposerine (SLP)

wherein $R^1$ and $R^2$ are each, independently, a linear, branched, saturated and/or unsaturated hydrocarbon, a cholesterol moiety, a steroid moiety, an aromatic moiety, a combination thereof, or a derivative thereof, and X is an O group or a $CH_2$ group. The asparagine derivative may include $R^1$ and $R^2$ groups that are the same or are different. In some embodiments the $R^1$ and/or $R^2$ group is a hydrocarbon of at least 5, 6, 7, 8, 9, 10, 11, 12, 13, 14, 15, 16, 17, 18, 19, 20 or more carbon units. The hydrocarbon may be a linear hydrocarbon or a saturated hydrocarbon. In certain embodiments, the chemical group represented by X can be an oxygen (O) group or a $CH_2$ group.

Certain embodiments include a method of synthesizing an asparagine, serine, or cysteine derivative or carboxylate salt thereof. In certain embodiments, methods of synthesizing an asparagine derivative or carboxylate salt thereof of the formula:

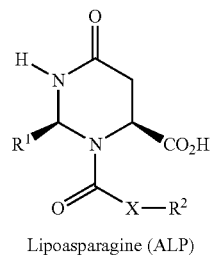

Lipoasparagine (ALP)

wherein $R^1$ and $R^2$ groups are each, independently, a linear, branched, saturated and/or unsaturated hydrocarbon, a cholesterol moiety, a steroid moiety, an aromatic moiety, a combination thereof, or a derivative thereof; and the chemical group X is an O group or a $CH_2$ group is contemplated. The methods include a) cylizing an asparagine, serine, or cysteine with a $R^1$-aldehyde under basic conditions; and b) reacting the cyclized asparagine, serine, or cysteine with a $R^2$-chloride, $R^2$-chloroformate or derivative thereof to produce an asparagine, serine, or cysteine derivative. The $R^1$, $R^2$, and X groups are as described above. In certain aspects, a phenyl chloroformate may be used as an acylating group. Substituting the phenoxide with an aliphaitc amine would provide urea analogs of the derivatives.

Various embodiments of the invention includes compositions and methods relating to a fatty asparagine, serine and/or cysteine derivatives. In certain embodiments, a cysteine derivative, or carboxylate salt thereof, of the formula:

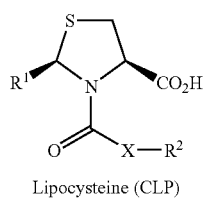

Lipocysteine (CLP)

wherein $R^1$ and $R^2$ are each, independently, a linear, branched, saturated and/or unsaturated hydrocarbon, a cholesterol moiety, a steroid moiety, an aromatic moiety, a combination thereof, or a derivative thereof. The cysteine derivative may include $R^1$ and $R^2$ groups that are the same or are different. In some embodiments the $R^1$ and/or $R^2$ group is a hydrocarbon of at least 5, 6, 7, 8, 9, 10, 11, 12, 13, 14, 15, 16, 17, 18, 19, 20 or more carbon units. The hydrocarbon may be a linear hydrocarbon or a saturated hydrocarbon.

In various embodiments the cysteine derivative may be comprised in a liposome, a surfactant, a detergent, an adjuvant, a food additive, or a food stuff.

Certain embodiments include a method of synthesizing a cysteine derivative or carboxylate salt thereof. In certain embodiments, methods of synthesizing a cysteine derivative or carboxylate salt thereof of the formula:

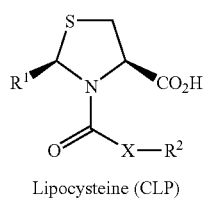

Lipocysteine (CLP)

wherein $R^1$ and $R^2$ groups are each, independently, a linear, branched, saturated and/or unsaturated hydrocarbon, a cholesterol moiety, a steroid moiety, an aromatic moiety, a combination thereof, or a derivative thereof. The methods include a) cylizing a cysteine with a $R^1$-aldehyde under basic conditions; and b) reacting the cyclized cysteine with a $R^2$-chloride, $R^2$-chloroformate or derivative thereof to produce a cysteine derivative. The $R^1$ and $R^2$ are as described above.

In various embodiments the asparagine, serine or cysteine derivative may be comprised in a liposome, a surfactant, a detergent, an adjuvant, a food additive, or a food stuff.

Various embodiments include an asparagine, serine, or cysteine derivative produced by the process comprising a) cylizing asparagine, serine, or cysteine with a fatty aldehyde under basic conditions; and b) reacting the cyclized asparagine, serine, or cysteine with a fatty acid chloride, chloroformate or a derivative thereof to produce a fatty asparagine, serine or cysteine derivative.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
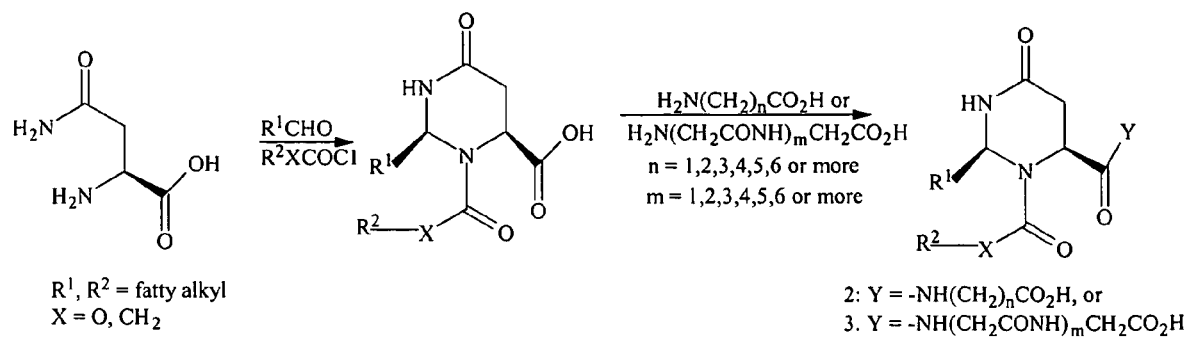
FIG. 1 illustrates an exemplary synthetic method for production of fatty asparagine derivatives including a tethering group.

Various embodiments of the invention provide methods and compositions related to the synthesis and use of fatty asparagine, serine and/or cysteine derivatives (also referred to as asparagine, serine, or cysteine derived lipopeptide (ALP, SLP or CLP, respectively, or lipoasparagine, liposerine or lipocysteine, respectively) or a carboxylate salt thereof. It is known that the acid salt of asparagine may be condensed with acetone to form a corresponding pyrimidone (Hardy and Samworth, 1977). In certain embodiments of the invention, a similar reaction is used with the exception that an aldehyde is used in place of acetone (Chu et al., 1992) followed by a subsequent reaction with a chloroformate. In certain embodiments of the invention, the aldehyde and chloroformate will typically contain, independent of each other, an $R^1$ or $R^2$ group, respectively. The composition of the aldehyde and chloroformate dictate the $R^1$ and $R^2$ groups incorporated into the exemplary fatty asparagine derivative (General Formula I or a carboxylic salt thereof) or the exemplary fatty cysteine derivative (General Formula II or a carboxylic salt thereof). In certain embodiments serine and cysteine may be substituted for asparagine without alteration of the chemistry described herein. The cyclization reaction may result in various substitutions on the heterocycle and these materials may be produced in either optical series.

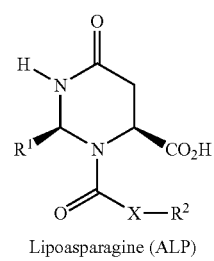

Lipoasparagine (ALP)

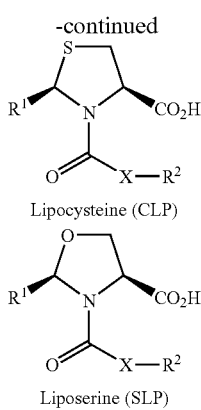

Lipocysteine (CLP)

Liposerine (SLP)

The $R^1$ and $R^2$ may be the same or different moieties. $R^1$ may be a linear, branched, saturated and/or unsaturated hydrocarbon of 5 or more carbon atoms. The hydrocarbon may be 5, 6, 7, 8, 9, 10, 11, 12, 13, 14, 15, 16, 17, 18, 19, 20, 21, 22, 23, 24, 25, 30, 35, or more carbon units in length. $R^1$ and/or $R^2$ may also include other derivatives such as cholesterol, steroids, aromatic groups and other hydrophobic molecules or molecules containing hydrophobic groups or derivatives thereof. $R^2$ may be a linear, branched, saturated and/or unsaturated hydrocarbon of 5 or more carbon atoms. The hydrocarbon may be 5, 6, 7, 8, 9, 10, 11, 12, 13, 14, 15, 16, 17, 18, 19, 20, 21, 22, 23, 24, 25, 30, 35, or more carbon units in length. $R^1$ and/or $R^2$ may also include other derivatives such as cholesterol, steroids, phenyl and other hydrophobic molecules or molecules containing hydrophobic groups.

GENERAL FORMULA 1

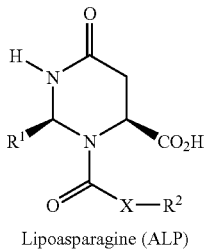

Lipoasparagine (ALP)

GENERAL FORMULA 2

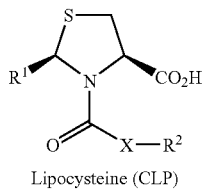

Lipocysteine (CLP)

GENERAL FORMULA 3

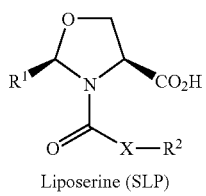

Liposerine (SLP)

I. Synthesis of Fatty Asparagine Derivatives.

In various embodiments of the invention, an asparagine, serine or cysteine is typically cyclized with a fatty aldehyde $R^1CHO$, where $R^1$ as described herein. The cyclized amino acid is reacted with a fatty acid chloride or fatty chloroformate, $R^2XCOCl$, where $R^2$ may be any of the groups described above and X is typically an oxygen or a $CH_2$.

For example, perhydropyrimidinones are synthesized according to the following exemplary scheme (Scheme 1).

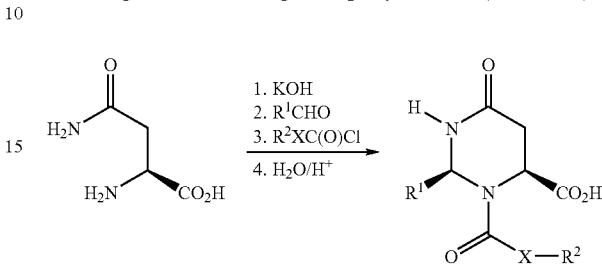

Briefly, D- or L-Asparagine monohydrate (1.0 g, 6.7 mmol), optionally cysteine or serine, is dissolved in KOH/MeOH solution (10 mL, 0.67 N) and treated with fatty aldehyde (1.0 equiv) for 24 hours at room temperature. Methanol is then removed by using a rotovap and high vacuum. The residue is suspended in 10 mL dioxane/20 mL 10% aqueous $Na_2CO_3$, stirred well, and chilled in an ice bath. With vigorous stirring, fatty acid chloride or chloroformate (1.0 equiv) dissolved in 10 mL dioxane is added by syringe dropwise. The reaction mixture is allowed to warm slowly to room temperature. After 16 hours, the solution is cooled in an ice bath and 3 mL 10% HCl is added slowly.

At this point, the product may precipitate. In some embodiments, it may be vacuum filtered and rinsed on a Buchner funnel with ice cold water and air dried.

If precipitation does not occur, the acidic solution may be extracted 3×20 mL with $Et_2O$. Combined organic layers are washed with brine, dried ($Na_2SO_4$), filtered and the solvents are evaporated. The residue is dried in a round bottom flask on high vacuum.

Flash chromatography may also be performed using 40 g silica gel and eluting with chloroform or ethyl acetate/hexanes.

In various embodiments, an ω-amino acid-tethered ALPs may be used to 1) form liposomes, 2) modulate liposome properties based on ALP structure, and 3) may be appended after liposomal formation with peptides ligands at the acid group. For example a human growth hormone (hGH) sequence may be appended and used as a peptide ligand. Additional examples of targeting ligands includes, but is not limited to, hormones, antibodies, cell-adhesion molecules, saccharides, drugs, and neurotransmitters. Exemplary targeting ligands are described in U.S. Pat. No. 6,287,857 (incorporated herein by reference). In addition, liposomes may bind to receptors and tissues using hGH surface-modified liposomes and RGD-modified liposomes, respectively, or other ligands. An ω-amino acid-tethered ALPs is an asparagine derivative that has been modified with a linker moiety to which other substituents may be coupled.

In certain embodiments, tethering molecules may be incorporated into the asparagine derivatives. Compounds such as $NH_2(CH_2)_nCO_2H$ and $NH_2(CH_2CONH)_mCH_2CO_2H$, where n and m are 1, 2, 3, 4, 5, 6, or more. Four-aminobutanoic acid may be attached under aqueous conditions using known peptide or protein coupling reagents, such as various bifunctional protein-coupling agents such as N-succinimidyl-3-(2-pyridyldithiol) propionate (SPDP), iminothiolane (IT), bifunctional derivatives of imidoesters (such as dimethyl adipimidate Hcl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene) (for exemplary methods see Corbett and Gleason, 2002). This conversion generates an ALP, CLP or SLP that is appended with a tether for various modifications such as surface modification for providing enhanced liposomal recognition, which may increase targeting efficiency of liposomes. Various compounds may be used as tethering molecules including, but not limited to amino acids, polypeptides, diamines, polyamines, amino alcohols, amino thiols, diols (e.g., oxiranes for linkage to the heterocycle carboxylic acid to provide an ester and ether linkage from a lipopeptide to a targeting group or other compound), thiol alcohol (e.g., using Episulfide for linkage to the heterocycle carboxylic acid to provide an ester linkages at a lipopeptide and a sulfur atom coupling to a targeting group or other compound), dithiols, or a combination thereof (for exemplary methods see U.S. Pat. No. 6,309,842 and Gianolio and McLaughlin, 2001)

II. Synthesis of Fatty Cysteine Derivatives.

In certain embodiments, a fatty cysteine derivative may be synthesized. For example, pyridine (1.0 mL) is added to a stirred slurry of cysteine (1.0 mmol) in 6.0 mL dioxane or THF. The mixture is stirred 1 hr after which the appropriate aldehyde (1.0 mL) is added dropwise. The mixture is heated to 45-50° C. and stirred overnight. The acid chloride (1.1 eq; neat for liquids, solid acid chlorides are dissolved in 3 mL dioxane prior to addition) is added with vigorous stirring. The mixture is stirred 24 h and EtOAc (5 mL) is added. The mixture is washed with 5% HCl (2×5 mL) and brine (2×5 mL). The organic layers are combined, dried with sodium sulfate, and evaporated. The desired product is isolated by gradient flash chromatography (silica gel, 15×the weight of the crude product; toluene, 15% EtOAc/toluene, 30% EtOAc/toluene). Yields of 25-60% were obtained using this protocol.

III. Synthesis of Fatty Serine Derivatives.

In certain embodiments, a fatty serine derivative may be synthesized. For example, pyridine (1.0 mL) is added to a stirred slurry of serine (1.0 mmol) in 6.0 mL dioxane or THF. The mixture is stirred 1 hr after which the appropriate aldehyde (1.0 mL) is added dropwise. The mixture is heated to 45-50° C. and stirred overnight. The acid chloride (1.1 eq; neat for liquids, solid acid chlorides are dissolved in 3 mL dioxane prior to addition) is added with vigorous stirring. The mixture is stirred 24 h and EtOAc (5 mL) is added. The mixture is washed with 5% HCl (2×5 mL) and brine (2×5 mL). The organic layers are combined, dried with sodium sulfate, and evaporated. The desired product is isolated by gradient flash chromatography (silica gel, 15×the weight of the crude product; toluene, 15% EtOAc/toluene, 30% EtOAc/toluene). Yields of 25-60% were obtained using this protocol.

IV. Methods of Using Fatty Aldehyde Derivatives

Amphiphilic molecules are typically used to produce emulsions. Emulsions are important throughout various industries in a wide-range of applications. Amphiphilic molecules of the present invention may be designed so beneficial physical properties that dictate the interaction of the molecules at hydrophilic/hydrophobic interfaces with each other and other molecules may be optimized for various uses. These uses include, but are not limited to the production of liposomes, detergents, food additives, gasoline additives, surfactants, organogels and the like. Compositions and methods of the present invention may be used in overcoming stability issues in paints, wax dispersions, cosmetics, food products, and other industrial applications using emulsions.

A. Liposomes

The presence of the inventive compounds in a lipid composition may enhance liposomal drug encapsulation, reduce the amount of the lipid carrier necessary for efficient entrapment of drugs, stabilize liposomal formulation of the drug (both in suspension and in a lyophilized powder), and target or direct liposomes within a subject or patient.

Certain embodiments of the invention include the synthesis and characterization of novel Asparagine derivative liposomal particles (ALPs) with diverse non-polar units as described herein (e.g., linear and branched alkyl, alkenyl, aryl, and steroidal groups). In addition, hydrophobic units containing selected polar functionalities (ethers, esters, and amides) and non-symmetrically substituted surfactants are also contemplated. These structural variants may be employed to examine the structure-function relationships and engineer liposomes with properties including, but not limited to optimal circulation, clearance, and content delivery (e.g., distereoylphosphatidylcholine liposomes (DSPCLs)).

In an exemplary embodiment of the invention, the use of novel lipoasparagines, lipocysteines and/or liposerines for engineering therapeutically useful liposome properties is contemplated, see below for more detail. Distereoylphosphatidylcholine liposomes (DSPCLs) employed in the examples provided are detergent bilayer vesicles. Recent interest in liposome technology is driven by its potential use as transport vehicles (>100-1000 nm diameter) for the delivery of diagnostic and therapeutic agents. The advantages of medicinal agent encapsulation in liposomes include: reduced toxicity due to decreased circulatory concentrations, improved stability of therapeutic agents in the liposome environment, and the potential for modulated or tissue-selective agent delivery. Unmodified liposomes tend to effect selectivity based on liposome composition and size. Desirable liposome properties may be achieved via detergent additives. Novel asparagine-, cysteine-, and/or serine-derived lipopeptide (ALPs, CLPs, and/or SLPs) surfactants as DSPCL additives may be employed to address various problems associated with liposome technology. For example: (1) enhancing content delivery properties via structural modifications of the ALP, CLP, and/or SLP and (2) the ability to chemically modify the surfaces of preformed, agent-loaded liposomes to enable tissue-selective targeting, as well as others. The former exploits the unique potential of ALPs, CLPs, and/or SLPs for structural diversity to enable an examination of structure-function relationships of ALP, CLP, and/or SLP containing liposomes, e.g., DSPCs (ALP-DSPCs). The latter exploits recent developments that afford efficient peptide bond formation in aqueous media to modify ALP-, CLP-, and/or SLP-liposomes that are preloaded with therapeutic agent(s). The therapeutic potential of liposomes may be enhanced in at least three ways: use of nontoxic and nonimmunogenic surfactants, improved liposome content delivery properties, and establishment of a general protocol for post-liposomal surface modification of off-the-shelf, preloaded liposomes for targeting to pre-selected tissues.

In various embodiments, the development of a technology that enables coupling of ALP, CLP, and SLP headgroups with ligands that bind to specific cell surface features are contemplated. For example, a peptide human growth hormone (hGH) ligand may be coupled to the isolated ALPs and ALP-DSPCs.

Other embodiments of the invention include coupling the ALP-, CLP-, and/or SLP-DSPCs to a tripeptide that is known to target human cancer cells for tissue-selective delivery of surface-modified DSPCs. Targeting may be verified by non-invasive imaging technology using liposomes preloaded with technetium-99m($^{99m}$Tc) or other known imaging agents.

The liposomes may be made from the lipopeptide derivatives alone or in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol. Synthetic phospholipids that may also be used, include, but are not limited to, dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Other additives such as cholesterol or other sterols, cholesterol hemisuccinate, glycolipids, cerebrosides, fatty acids, gangliosides, sphingolipids, 1,2-bis(oleoyloxy)-3-(trimethylammonio)propane (DOTAP), N-[1-(2,3-dioleoyl)propyl]-N,N,N-trimethylammonium (chloride) (DOTMA), D,L,-2,3-distearoyloxypropyl(dimethyl)-.beta.-hydroxyethyl ammonium (acetate), glucopsychosine, or psychosine can also be added, as is conventionally known. The relative amounts of phospholipid and additives used in the liposomes may be varied if desired. The preferred ranges are from about 80 to 95 mole percent phospholipid and 5 to 20 mole percent lipoasparagine, lipocysteine, liposerine or other additive. Cholesterol, cholesterol hemisuccinate, fatty acids or DOTAP may be used in amounts ranging from 0 to 50 mole percent (see U.S. Pat. No. 6,448,392, incorporated herein by reference, for exemplary methods and compositions).

B. Detergents

Detergents and soaps are typically made from special molecules comprising a hydrocarbon chain (which is hydrophobic) with a polar 'hydrophilic' headgroup. Water is a polar solvent; so the polar end of the molecule buries itself in the polar solvent. The hydrophobic end of the molecule sticks out to avoid contact with the water; a film of molecular thickness is formed.

Because the surface of the water is coated with hydrophobic molecules, it behaves very differently. Pure water has a high surface tension. This high surface tension is a consequence of the strong interaction between the molecules; these interactions mean that the liquid is driven to reduce its surface area as much as possible, because when molecules are at the surface they experience less attraction from neighboring molecules. Films of soap molecules that form at the surfaces have a dramatically lower surface tension; the hydrophobic molecules interact with each other much less than do the water molecules. They can easily form structures like bubbles with high surface areas. It is the relative sizes of the molecular forces between the molecules in soaps and detergents and those of water that allow one to blow soap bubbles.

Amphiphilic molecules may also cluster together in an aqueous solution, with the hydrophobic component of the molecule pointing inwards, and the hydrophilic pointing outwards. Formation of these micelles may also help to capture other molecules, for example the molecules of fats and greases which are hydrophobic; they play an important role in detergency actions, as well as lipophilic drugs or compounds that are not readily soluble in water.

Hydrophobic interactions of amphiphilic molecules may also form double layer structures in which the hydrophobic parts of the amphiphilic molecules on neighboring layers point inwards, but instead of rolling up into a ball as in the micelles, they line up in a bi-layer. By far the most important context in which such layers are formed is in living matter. Membranes are vitally important structures in living organisms. Cells are bounded by membranes, as is the nucleus. These membranes are essentially double layers. Membranes, as well as playing a structural role, also must allow certain molecules to pass through them.

C. Adjuvants Antigens may be incorporated into liposomes by the dehydration-rehydration vesicle method using different membrane compositions and the co-encapsulation of immunostimulants. Antigens may be encapsulated into liposomes formed from compounds of the present invention, a mixture of phospholipids and/or cholesterol. The preparations may be characterized in relation to stability, toxicity and the protection of animal models against the antigen after immunization. Liposome preparations may be quite stable, retain originally encapsulated antigen for prolonged periods time ranging from days, weeks, months, and years. The liposomes will typically be associated with immunostimulants, adjuvants, and other excipients.

D. Food Additives

Various food stuffs, for example milk, are oil-in-water emulsion, with the fat globules dispersed in an aqueous solution. The amphiphilic properties of the instant invention may be used to alter the properties of emulsified fats in a variety of food products.

E. Gasoline Additives

The demand for high-quality fuels has resulted in the use of many different additives which are introduced to the gasoline at refineries and product terminals. Additives injected at the refinery are designed to help the product meet American Society for Testing and Materials gasoline specifications, provide retail brand differentiation and meet the individual requirements of multiple customers.

Gasoline additives are typically designed to perform a wide variety of specific functions. The two broad applications of gasoline additives are: 1) to meet specifications whether external or internal, protect distribution systems and automotive parts and meet possible competitive gasoline performance and 2) to provide an advantage to gasoline, particularly for advertising purposes, by differentiating one product from another, or making a common product into a unique product.

Various classes of additives include additives such as anti-knock, corrosion inhibitor and antioxidant additives. Performance additives include detergents, dispersants, anti-icers, combustion enhancers/modifiers, fluidizer oils and flow improvers. All these additives improve either fuel or engine efficiency or durability. Within the category of performance additives, detergents and dispersants are known collectively as deposit control additives.

Detergents help to remove dirt and deposits (gums, varnish, carbon deposits) from an engine to keep it running according to original specifications. In recent years, nearly all car makers have switched from carburated fuel systems to fuel injection systems.

Fuel systems are more finely tuned to minimize emissions, but they're far less tolerant of dirt and deposits. This has made gasoline detergency a matter of increasing importance in vehicle performance. The nationally recommended level of detergency is designed to prevent deposits from forming on intake valves and fuel injectors, and higher levels have been shown to actually remove some accumulated deposits.

F. Surfactants

A surfactant is typically defined as a material that can greatly reduce the surface tension of water when used in very low concentrations. A particular type of molecular structure performs as a surfactant. This molecule is made up of a water soluble (hydrophilic) and a water insoluble (hydrophobic) component. The hydrophobic portion is usually the equivalent of an 8 to 18 carbon hydrocarbon, and can be aliphatic, aromatic, or a mixture of both. The sources of hydrophobic portions of the molecule are normally natural fats and oils, petroleum fractions, relatively short synthetic polymers, or relatively high molecular weight synthetic alcohols. The hydrophilic groups give the primary classification to surfactants, and are anionic, cationic and non-ionic in nature. The anionic hydrophiles are the carboxylates (soaps), sulphates, sulphonates and phosphates. The cationic hydrophiles are some form of an amine product. The non-ionic hydrophiles associate with water at the ether oxygens of a polyethylene glycol chain. In each case, the hydrophilic end of the surfactant is strongly attracted to the water molecules and the force of attraction between the hydrophobe and water is only slight. As a result, the surfactant molecules align themselves at the surface and internally so that the hydrophile end is toward the water and the hydrophobe is squeezed away from the water.

Because of this characteristic behavior of surfactants to orient at surfaces and to form micelles, all surfactants perform certain basic functions. However, each surfactant excels in certain functions and has others in which it is deficient.

Foaming agents, emulsifiers, and dispersants are surfactants which suspend respectively, a gas, an immiscible liquid, or a solid in water or some other liquid. Although there is similarity in these functions, in practice the surfactants required to perform these functions differ widely. In emulsification, as an example, the selection of surfactant or surfactant system will depend on the materials to be used and the properties desired in the end product. An emulsion can be either oil droplets suspended in water, an oil in water (O/W) emulsion, water suspended in a continuous oil phase, water in oil (W/O) emulsion, or a mixed emulsion. Selection of surfactants, orders of addition and relative amounts of the two phases determine the class of emulsion.

Each of these three functions is related to the surfactant absorbing at a surface, either gas, liquid or solid with the hydrophilic ends of the molecules oriented to the water phase. The surfactants form what amounts to a protective coating around the suspended material, and these hydrophilic ends associate with the neighboring water molecules. In addition to surfactant effects the stability of these suspensions is related to the particle size and density of the suspended material.

Solubilization is a function closely related to emulsification. As the size of the emulsified droplet becomes smaller, a condition is reached where this droplet and the surfactant micelle are the same size.

At this stage, an oil droplet can be imagined as being in solution in the hydrophobic tails of the surfactant and the term solubilization is used. Emulsions are milky in appearance and solubilized oils, for example, are clear to the eye.

Surfactant replacement therapy in the neonate.—Natural, endogenous surfactant is a compound composed of phospholipids, neutral lipids, and proteins (Jobe, 1986; Berry, 1991; Avery and Mead, 1959; von Neergard, 1929; Hallman et al., 1987) that forms a layer between the alveolar surface and the alveolar gas and reduces alveolar collapse by decreasing surface tension within the alveoli. Surfactant deficiency is almost always associated with the formation of hyaline membranes in the immature lung and the onset of respiratory distress syndrome (RDS)-a major cause of morbidity and mortality in premature infants.(Avery and Mead, 1959) Without surfactant, alveoli may never inflate or may collapse on expiration and require inordinate force to re-expand on inspiration, leading to the development of RDS (Avery and Mead, 1959; Hallman et al., 1987). The incidence of RDS is related more to lung immaturity than to gestational age (Stableman, 1975). However, in general, the more premature the infant, the less the surfactant production and the higher the probability for RDS (von Neergard, 1929; Stableman, 1975) Direct tracheal instillation of surfactant has been shown to reduce mortality and morbidity in infants with RDS (Horbar et al., 1993; Lang et al, 1990; Hoekstra et al., 1991; Kattwinkel et al., 1993; Merritt et al., 1991; Dunn et al., 1991; Long et al., 1991a; Liechty et al., 1991; Long et al, 1991b; Fujiwara et al., 1990; The OSIRIS Collaborative Group, 1992; Ferrara et al., 1994; Hallman et al., 1985; Berry et al., 1994; Gortner et al., 1992; Corbet et al., 1991a; Bose et al., 1990; Corbet et al., 1991b; Merritt et al., 1986).

Surfactant can be extracted from animal lung lavage and from human amniotic fluid or produced from synthetic materials. Two basic strategies for surfactant replacement have emerged: (1) prophylactic or preventive treatment in which surfactant is administered at the time of birth or shortly thereafter to infants who are at high risk for developing RDS and (2) rescue or therapeutic treatment in which surfactant is administered after the initiation of mechanical ventilation in infants with clinically confirmed RDS.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

ALP and ALP-Tether Preparations

Two ALPs were assembled using laurylaldehyde and either stearic acid chloride or cetyl chloroformate ($R=C_{11}H_{23}$, $R'=C_{16}H_{33}$, $X=O$ and $CH_2$). The preparations occurred in one pot and in good yields. The pathway depicted in FIG. 1 is amenable to sterically hindered aldehydes and may be deployed with aryl and $\alpha,\beta$-unsaturated aldehydes, though, the later group leads to conjugate additions in hydroxylic solvents (that may be used to explore analogs that have polar components). The ability to install each fatty unit independently readily affords the capability of examining the influence of non-symmetrically fitted hydrophobic units.

Molecular modeling of a distearoyl derivative using MM2 energy minimization illustrates the expected conformation of lipoasparagines/ALPS in which the fatty tails are roughly parallel and the carboxylate is exposed on one face. Varying the aldehyde and acid chloride/chloroformate provides access to a wide range of derivatives that enables preparation of various structure, lipid derivative, and/or liposome property relationships in an unprecedented way. The hydrophobic substituents may be of different lengths and may possess branching, aromatic units, steroidal moieties, and the like. Some of the various properties of interest are liposome stability to temperature and pH, ease of ligand attachment, and in vivo toxicity.

The compounds of the invention are capable of unprecedented structural diversity necessary for a broad range of surfactant non-polar units. Omega aminohexanoic acid in THF has been attached using N-hydroxysuccinimide as the activating agent. This conversion is indicative of the ability for post-liposomal modification and generation of a prototype ALP that is appended with an appropriate tether for surface modification and enhanced recognition.

Example 2

Post-Liposomal Modification with Ligand and Characterization

To maximize the breadth and ease of applications, it would be advantageous to construct the liposome with a few percent lipoasparagine, either with or without linker attached, and then to modify the outer surface by covalent attachment of ligand. To accomplish this, liposomes will be manufactured with lipoasparagine unmodified and modified with linkers of various lengths. Then in aqueous suspension, a ligand is attached. Standard procedures can be utilized for this purpose, taking advantage of the carboxyl end group in each case.

Example 3

Liposome Preparations

Two ALPs of General Formula 1 were prepared, a) laurylaldehyde (X=O and $R^1$, $R^2=C_{11}H_{23}$) or b) (S,S)-(3-Octadecanoyl-6-oxo-2-undecyl-hexahydro-pyrimidine-4-carboxlic acid and tested for the ability to form liposomes and for its suitability as a component of liposomes containing phospholipids and cholesterol. Liposomes were prepared by mixing varying amounts of the phospholipid, distearoyl phosphatidylcholine (DSPC), cholesterol or ALP in chloroform. The chloroform was removed to form a thin lipid film. After vacuum desiccation overnight, each lipid formulation was rehydrated with phosphate buffered saline (PBS), pH 7.2, warmed to 55° C. (phase transition temperature of DSPC) and vortexed vigorously to form multilamellar liposomes (MLV). Aliquots of each MLV formulation were set aside and observed by light microscopy. DSPC MLV, DSPC MLV containing 10 mole % ALP, ALP lipid structures (3 mg/ml) and ALP lipid structures (30 mg/ml), respectively, were imaged. The DSPCL image shows the classical globular MLV structure. Inclusion of 10% ALP did not appear to disturb the formation of MLV, in fact the MLVs were easier to process in the presence of ALP. ALP at low concentrations typically form liposomes, whereas at high concentrations, crystal structures were evident.

Figure 2:
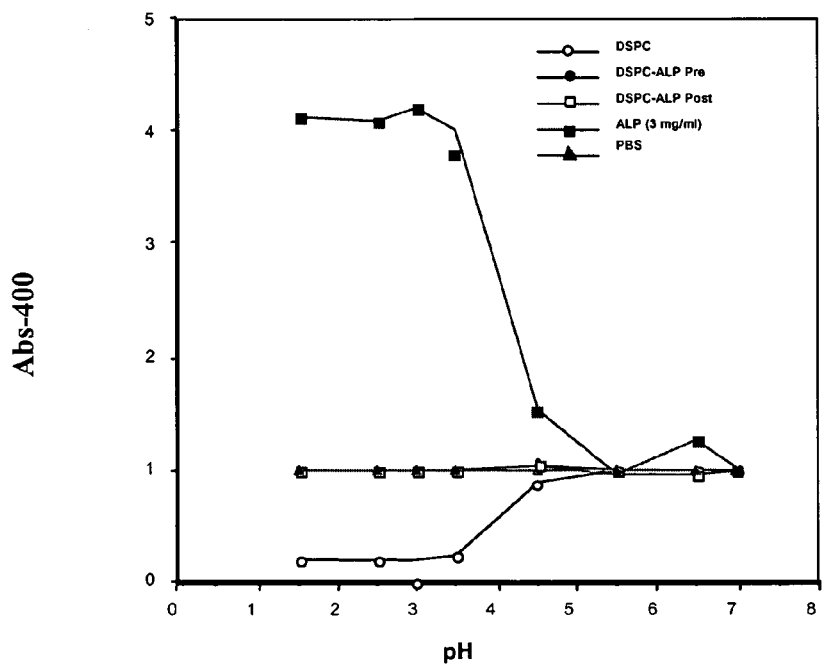
FIG. 2 illustrates the absorbance change as a function of pH titration. Samples (50 µl) in 3 ml of PBS were titrated with HCl. The pH was measured and absorbence read at 400 nm.

The DSPC MLV samples were then processed by extrusion to form liposomes with diameters of 100 nm. The pH sensitivity of the liposomes were compared by monitoring turbidity at 400 nm as a function of pH. FIG. 2 depicts an exemplary pH titration result using (S,S)-(3-Octadecanoyl-6-oxo-2-undecyl-hexahydro-pyrimidine-4-carboxlic acid, an exemplary ALP. There was a significant decrease in the absorbance for the DSPCL sample between pH 4.5 to 3.5 suggestive of liposome disaggregation to the component surfactants. In contrast, the absorbance of the ALP sample alone increased as the pH was lower from 4.5 to 3.5, indicating the sample aggregated or fused into larger structures. Interestingly, the extruded DSPC-ALP samples showed very little change in the absorbance measurements as a function of pH, suggesting that ALP significantly modulated the pH sensitivity of liposomes. This feature of ALP may be useful in certain applications where pH plays a role.

Example 4

Material and Methods

Synthesis and Characterization of ALPs.

For these studies, 6-aminohexanoic acid tethered analogs are employed for temperature and pH stability studies. Non-polar region modified ALPs with variable lipophilic portion lengths, branching, unsaturation and steroid and aryl units will be incorporated into liposomes at three concentrations the resulting vesicles will be tested. Analogs that are amides at the secondary amine will be prepared as previously described and examined. Carbamate analogs will be prepared via coupling with chloroformates of the corresponding alcohols. In further studies, ω-amino acid tethers and glycine-based tethers will be examined in studies to determine optimal analogs for both post-liposomal modification and ligand-receptor binding. Since ω-amino acids are commercially available in a complete series of carbon lengths, the effects of linker length may be explored. Also, an oligoglycine analog will be examined that has an identical number of intervening atoms between the amino and carboxyl units as the ω-amino acid analog with the most desirable properties (expected optimal length n=2).

Preparation and Characterization of ALP-containing Liposomes.

Depending on the desired liposome formulation, thin lipid films are prepared from each ALP as previously described. Extruded liposomes are washed and concentrated by ultracentrifugation (41,000 rpm). Liposome pellets are resuspended in PBS and stored at 4° C. until needed for conjugation. Liposome diameter is determined by laser light particle scattering. Ultrastructure of liposomes is determined by electron microscopy. Phospholipid content is determined by colorimetric assay (Stewart, 1980). The amount of ALP incorporated is estimated by alcian blue dye (Gold, 1981; Feuerstein et al., 1984; Whiteman, 1973). The pH sensitivity of the liposomes will be determined by turbidity following pH titration and calcein dye leakage (Drummond et al., 2000). To verify the incorporation of ALPs in liposome preparations and investigate post-liposomal coupling of 4-amino-1,1'-azobenzene-3,4'-disulfonic acid is examined. Gel-filtration will provide dye-coupled liposome. HPLC analysis and comparison with prepared standards will determine the original extent of liposome-dye covalent attachment. ALP-liposomes for technetium-99 m ($^{99m}$Tc) labeling studies will be prepared in the same manner except the PBS buffer will contain 200 mM glutathione (GSH). The presence of GSH in the liposome interior is needed for $^{99m}$Tc-labeling (Phillips, 1992).

Ligand-Receptor Binding Studies.

Receptor-binding potencies studies are employed to quantitatively determine optimal tether lengths and compositions (Table 1, analogs 2a,2i-k,3a). Monomeric ALPs and ALP containing-liposomes are modified with hGH peptide as described above. Beginning with compound 2a, comparative binding strengths are measured using standard in vitro GH radioreceptor assays. Measurement of the equilibrium binding constants (Keq) of the monomeric ALP-hGH peptide and liposomes containing the ALP-hGH peptide to: (i) somatogen receptors in a human liver GH radioreceptorassay; (ii) lactogen receptors in a radioreceptorassay for lactogenic hormones; and (iii) receptors in Nb2 Lymphoma cells will be performed. Further binding studies will examine how tether length influences binding. Finally, examination of the binding of 3a which substitutes a water soluble tether of identical atom length to the ω-amino acid that is expected to be of optimal length. Compounds such as $NH(CH_2)_nCO_2H$ and $NH(CH_2CONH)_mCH_2CO_2H$, where n and m are 1, 2, 3, 4, 5, 6, or more. Four-aminobutanoic acid may be attached under aqueous conditions using N-hydroxysuccinamide or other activating agents

TABLE 1

| Analog | $R^1$ | $R^2$ | X | M (length of ($CH_2CONH$) linker) | N (length of ($CH_2$) linker) |
|---|---|---|---|---|---|
| 1a | C12 | C5 | CH2 | — | — |
| 2a | C17 | C5 | CH2 | 5 | — |
| 2b | C17 | C12 | CH2 | 5 | — |
| 2c | C18 | C18 | CH2 | 5 | — |
| 2d | C12 | C15* | CH2 | 5 | — |
| 2e | C12 | C15** | CH2 | 5 | — |
| 2f | C12 | C2H4-phenyl | CH2 | 5 | — |
| 2g | C12 | C2H4-naphthyl | O | 5 | — |
| 2h | C12 | Estradiol | O | 5 | — |
| 2I | C17 | C5 | CH2 | 1 | — |
| 2j | C17 | C5 | CH2 | 4 | — |
| 2k | C17 | C5 | CH2 | 7 | — |
| 3a | C17 | C5 | CH2 | — | 2 |

Targeting of RGD-ALP-Liposomes to B16 Melanoma Cells

Varying amounts of 99mTc-RGD-ALP-liposomes or plain 99mTc-liposomes are incubated with the cells. Following centrifugation and washing, the 99mTc-activity with the cells is quantitated and binding curves generated.

Quantitate the Ability of RGD-ALP-Liposomes Encapsulating Technetium-99m to Target B16 Melanoma in Mice Using Non-Invasive Imaging ALP-liposomes for these studies encapsulate glutathione for 99mTc-labeling methods. Attachment of the RGD peptide to the liposomes is carried out as described above. Mice with B16 tumors (n=6/group) will be anesthetized and injected i.v. with 99mTc-RGD-ALP-liposomes or plain 99mTc-liposomes. Gamma camera images will be acquired at various time points. Analysis of these images will allow quantitation of the percentage of RGD-ALP-liposomes in the tumor and determination of the target-to-background ratio. At 24 hours post-injection, the mice will be euthanized and tissues collected for tissue biodistribution determination. Radioactivity per gram of tissue and radioactivity per organ will be calculated. Values will be reported as mean±SEM. Student's unpaired t-test will be used to compare differences in the radioactivity per gram of tissue and radioactivity per organ as a function of time and 99 mTc-liposome agent injected.

Example 5

Characterization of Asparagine and Cysteine Lipopeptides

GENERAL FORMULA 1

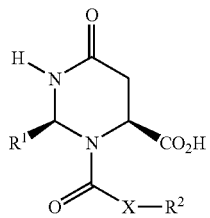

Lipoasparagine (ALP)

Data for Representative Asparagine Lipopeptides

General Formula 1 (ALP), $R^1=C_{11}H_{21}$, $X=CH_2$, $R^2=C_{16}H_{33}$: mp=93 °C.; TLC (silica gel, ethyl acetate) rf=0.45; $^1H$ NMR ($CDCl_3$) δ 0.89 apparent t, 6H), 1.15-1.4(m, 48 H), 1.58-1.70 (m, 2H); 1.70-1.90 (m, 2H), 2.30-2.50 (m, 2H), 2.76-3.10 (m, 2H), 4.91-5.17 (m, 1.6H); smaller signals at 4.7 (m, 0.2H) and 5.8 (m, 0.2H) apparently correspond to amide rotomers. $^{13}$CNMR ($CDCl_3$) δ 14.0, 22.0, 24.4, 24.6, 24.9, 25.2, 28.5, 28.6, 28.6, 28.7, 28.8, 29.0, 29.2, 29.3, 31.2, 31.2, 31.7, 32.1, 32.2, 35.6, 36.9, 166.1, 167.4, 170.4, 171.6, 172.2, 173.0.

General Formula 1 (ALP), $R^1=C_8H_{17}$, $X=CH_2$, $R^2=C_{16}H_{33}$: TLC (silica gel, ethyl acetate) rf=0.40; $^1H$ NMR ($CDCl_3$) δ 0.90 apparent t, 6H), 1.19-1.41 (m, 48 H), 1.58-1.70 (m, 2H); 1.70-1.90 (m, 2H), 2.30-2.50 (m, 2H), 2.76-3.10 (m, 2H), 4.91-5.01 (m, 1H), 5.02-5.17 (m, 1H); smaller signals at 4.7 (m, 0.2H) and 5.8 (m, 0.2H) apparently correspond to amide rotomers. $^{13}$CNMR ($CDCl_3$) δ 14.1, 21.0, 22.9, 25.5, 26.0, 25.9, 29.6, 29.8, 29.9, 30.0, 31.5, 32.2, 34.8, 38.0, 52.0, 61.0, 64.0, 66.0, 70.0, 170.1, 170.8, 172.3, 172.6, 172.8, 174.3.

Data for Representative Cysteine Lipopeptides

GENERAL FORMULA 2

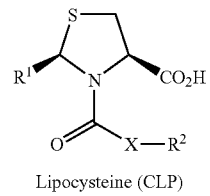

Lipocysteine (CLP)

General Formula 2 (CLP), $R^1=C_{11}H_{21}$, $X=CH_2$, $R^2=C_{16}H_{33}$: TLC (silica gel, 50% hexanes/ethyl acetate) rf=0.40); $^1H$ NMR ($CDCl_3$) δ 0.86 apparent t, 6H), 1.2-1.4 (m, 46 H), 1.6-2.85 (m, 4H); 2.22 (m, 1H), 2.40 (m, 1H), 3.27 (m, 1H), 3.45 (m, 1H), 4.92 (m, 2H), small signals at 4.80 (m, 0.2H) and 5.40 (m, 0.2H) apparently correspond to amide rotomers.

General Formula 2 (CLP), $R^1=C_9H_{19}$, $X=CH_2$, $R^2=C_{16}H_{33}$: TLC (silica gel, 50% hexanes/ethyl acetate) rf=0.38); $^1H$ NMR ($CDCl_3$) δ 0.89 apparent t, 6H), 1.2-1.4 (m, 42 H), 1.6-2.85 (m, 4H); 2.0-2.55 (m, 2H), 3.35 (m, 1H), 3.44 (m, 1H), 4.96 (m, 2H), 7.38 (broad singlet, 1H), small signals at 4.80 (m, 0.2H) and 5.40 (m, 0.2H) apparently correspond to amide rotomers.

General Formula 2 (CLP), $R^1=C_8H_{17}$, $X=CH_2$, $R^2=C_4H_9$: TLC (silica gel, 50% hexanes/ethyl acetate) rf=0.31); $^1H$ NMR ($CDCl_3$) δ 0.88 apparent t, 6H), 1.2-1.4 (m, 16 H), 1.6-1.85 (m, 4H); 2.40 (m, 1H); 2.46 (m, 1H); 3.31 (m, 1H), 3.58(m, 1H),3.44 (m, 2H), 4.96 (m, 2H), 7.38 (broad singlet, 1H), small signals at 4.81 (m, 0.2H) and 5.41(m, 0.2H) apparently correspond to amide rotomers.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,287,857
U.S. Pat. No. 6,309,842
U.S. Pat. No. 6,448,392
Avery and Mead, *Am. J Dis. Child*, 97:517-523, 1959.
Bangham et al., *J Mol. Biol.*, 13(1):253-259, 1965.
Berry, *Clin. Pediatr.*, 30(3):167-170, 1991.
Berry et al., *J. Pediatr.*, 124(2):294-301, 1994.
Bose et al., *J. Pediatr.*, 117:947-953, 1990.
Chue et al., *J. Am. Chem. Soc.*, 114:1800-1812, 1992.
Corbet et al., *J Paediatr. Child Health*, 27(4):245-249, 1991a.
Corbet et al., *J Pediatr.*, 118(2):277-284, 1991b.
Corbett and Gleason, *Tetrahedron Letters*, 43:1369-1372, 2002.
Drummond et al., *Prog. Lipid Res.*, 39:409-460, 2000.
Dunn et al., *Pediatr.*, 87(3):377-386, 1991.
Gianolio and McLaughlin, Bioorg. Med. Chem., 9(9):2329-23234, 2001.
Ferrara et al., *J Pediatr.*, 124(1):119-124, 1994.
Feuerstein et al., *Clinica Chimica Acta*, 144:249-253, 1984.
Fujiwara et al., *Pediatr.*, 86(5):753-764, 1990.
Gold, *Biochim. Biophys. Acta*, 673:408-415, 1981.
Gortner et al., *Pediatr. Pulmonol.*, 14(1):4-9, 1992.
Hallman et al., *J. Pediatr.*, 106(6):963-969, 1985.
Hallman et al., *J. Perinat. Med.*, 15:463-468, 1987.
Hardy and Samworth, *J. Chem. Soc.* [Perkin 1](17):1954-1960, 1977.
Hoekstra et al., *Pediatr.*, 88(1):10-18, 1991.
Horbar et al., *Pediatr.*, 92(2):191-196, 1993.
Jobe, *Respir. Care*, 31(6):467-476, 1986.
Kattwinkel et al., *Pediatr.*, 92(1):90-98, 1993.
Lang et al., *J. Pediatr.*, 116(2):295-300, 1990.
Liechty et al., *Pediatrics*, 88(1):19-28, 1991.
Long et al., *N. Engl. J. Med.*, 325(24):1696-1703, 1991a.
Long et al., *J. Pediatr.*, 118(4):595-605, 1991b.
Merritt et al., *J. Pediatr.*, 118(4):581-594, 1991.
Merritt et al., *N. Engl. J. Med.*, 315(13):785-790, 1986.
Phillips et al., *Nucl. Med. Biol.*, 19:539-547, 1992.
Stableman, In: *Neonatology*, Avery (Ed.),. Philadelphia, J. B. Lippincott, 221-249, 1975.
Stewart, *Anal. Biochem.*, 104: 10-14, 1980.
The OSIRIS Collaborative Group, Lancet, 340(8832):1363-1369, 1992.
von Neergard et al., *Ges. Exp. Med.*, 66:373, 1929.
Whiteman, *Biochem. J.*, 131:351-357, 1973.

What is claimed is:

1. A fatty amino acid compound, wherein the fatty amino acid compound or carboxylate salt thereof has a formula of:

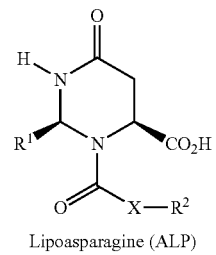

Lipoasparagine (ALP)

wherein $R^1$ and $R^2$ are each, independently, a linear, branched, saturated and/or unsaturated hydrocarbon, or a combination thereof, wherein $R^1$ is a hydrocarbon of at least 5 carbon units; and X is an O group or a $CH_2$ group.

2. The fatty amino acid compound of claim 1, wherein $R^1$ and $R^2$ are the same.

3. The fatty amino acid compound of claim 1, wherein $R^1$ and $R^2$ are the different.

4. The fatty amino acid compound of claim 1, wherein $R^1$ and $R^2$ are a hydrocarbon of at least 5 carbon units.

5. The fatty amino acid compound of claim 4, wherein the hydrocarbon is a linear hydrocarbon.

6. The fatty amino acid compound of claim 4, wherein the hydrocarbon is a saturated hydrocarbon.

7. The fatty amino acid compound of claim 4, wherein at least one of $R^1$ and $R^2$ is a linear saturated hydrocarbon of at least 10 carbon units.

8. The fatty amino acid compound of claim 7, wherein at least one of $R^1$ and $R^2$ is a linear saturated hydrocarbon of at least 15 carbon units.

9. The fatty amino acid compound of claim 8, wherein at least one of $R^1$ and $R^2$ is a linear saturated hydrocarbon of at least 20 carbon units.

10. The fatty amino acid compound of claim 1, wherein X is an O group.

11. The fatty amino acid compound of claim 1, wherein X is a $CH_2$ group.

12. A liposome comprising the fatty amino acid compound of claim 1.

13. A food comprising the fatty amino acid compound of claim 1.

* * * * *